US00PP29431P2

(12) United States Plant Patent
Hansen

(10) Patent No.: US PP29,431 P2
(45) Date of Patent: Jun. 26, 2018

(54) **X *MANGAVE* PLANT NAMED 'INKBLOT'**

(50) Latin Name: ***x Mangave×Manfreda* hybrid**
Varietal Denomination: Inkblot

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days. days.

(21) Appl. No.: 15/530,441

(22) Filed: Jan. 13, 2017

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373, 372
CPC ..... A01H 5/12
See application file for complete search history.

*Primary Examiner* — Kent L Bell

(57) ABSTRACT

A new and unique ×*Mangave* plant named 'Inkblot' characterized by long, horizontal to arching, dark green foliage with typically overlapping, irregular burgundy spotting. Leaf margin has soft lavender purple teeth. The flowers are light wine-colored with long divergent filaments and style and generate a large volume of nectar that is highly attractive to hummingbirds.

1 Drawing Sheet

Botanical classification: ×*Mangave* times *Manfreda* hybrid.

Variety denomination: 'Inkblot'.

BACKGROUND OF THE INVENTION

The present invention relates to the new and distinct ×*Mangave* hybrid plant, ×*Mangave* 'Inkblot' hybridized by the inventor at a wholesale perennial nursery in Zeeland, Mich., USA as cross between ×*Mangave* 'Bloodspot' (not patented) as the female or seed parent times *Manfreda* 'Chocolate Chips' (not patented) as the male or pollen parent. The cross was performed on Dec. 26, 2011, seeds were harvested, and sown on Aug. 8, 2012. Through trials at the same nursery the plant was originally assigned the breeder code XMANG-12-08-05. The new plant has been successfully asexually propagated initially by division at the same nursery in Zeeland, Mich. and also by sterile shoot-tip tissue culture. Both methods of asexual propagation systems have been found to produce stable and identical plants that maintain all the unique characteristics of the original plant.

No plants of ×*Mangave* 'Inkblot' have been sold, under this or any name, in this country or anywhere in the world, prior to the filing of this application, nor has any disclosure of the new plant been made prior to the filing of this application with the exception of that which was disclosed or sold within one year of the filing of this application, and was either derived directly or indirectly from the inventor.

BRIEF SUMMARY OF THE INVENTION

×*Mangave* 'Inkblot' differs from its parents as well as all other *Manfreda, Agave* and ×*Mangave* known to the applicant. The most similar known cultivars are ×*Mangave* 'Moonglow' U.S. Plant patent application Ser. No. 15/330,178 and ×*Mangave* 'Pineapple Express' U.S. Plant Pat. No. 28,613. Compared with 'Moonglow' the new plant has longer, more arching foliage of more green and less silver-blue, and smaller burgundy spotting. Compared to 'Pineapple Express' the new plant has longer and broader leaves that project outward and arch below the base when grown in containers. Compared with the female parent 'Bloodspot' the new plant has thinner, longer and broader foliage with the new plant also having wider and darker green undertone foliage. Compared with the male parent *Manfreda* 'Chocolate Chips' the new plant has less undulated, broader foliage with more silvery-blue base coloration and thicker.

The new plant, 'Inkblot', is unique from all of the above cultivars and all *Agave,* ×*Mangave* and *Manfreda* known to the inventor by the following combined traits:

1. Long, horizontal to slightly arching, nearly flat, dark green foliage.
2. Foliage develops heavy, irregular, typically-overlapping burgundy spots throughout upper and lower surfaces;
3. Teeth and apices on leaves are soft and flexible.
4. Moderate to rapid growth rate with good natural side shoot production;
5. Light wine-color flowers with long filaments and style on stiff, tall scapes.

BRIEF DESCRIPTION OF THE DRAWINGS

The photographs of ×*Mangave* 'Inkblot'; demonstrate the overall appearance of the new plant including the unique traits as a two-year old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
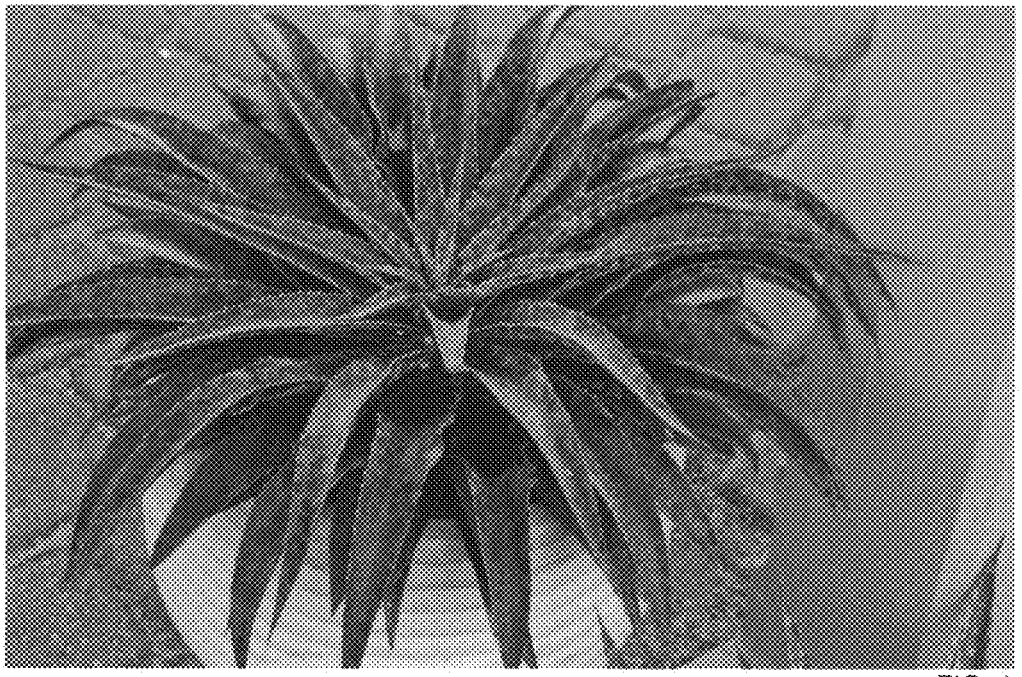
FIG. 1 shows the new plant having been grown in a container.
Figure 2:
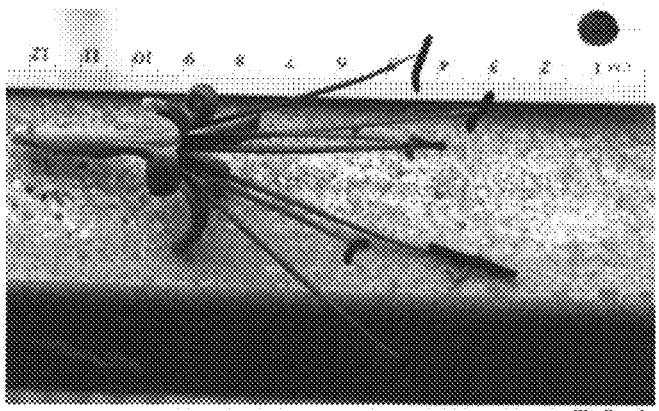
FIG. 2 shows a close-up of the flower.

The following descriptions and color references are based on the 2001 edition of The Royal Horticultural Society Colour Chart except where common dictionary terms are used. The new plant, ×*Mangave* 'Inkblot', has not been observed under all possible environments. The phenotype may vary slightly with different environmental conditions, such as temperature, light, fertility, moisture and maturity levels, but without any change in the genotype. The following observations and size descriptions are of a two-year old plant in a commercial wholesale greenhouse in Zeeland, Mich. with supplemental water and fertilizer as needed.

Parentage: ×*Mangave* 'Bloodspot' as female (seed) parent and *Manfreda* 'Chocolate Chips' as male (pollen) parent;

Propagation: Division of side shoots and sterile shoot-tip tissue culture;

Time to initiate roots from tissue culture: About 21 days;

Growth rate: Moderate to rapid;

Crop time: About 12 to 14 weeks to finish in a 3.8 liter container from a 35 mm tissue culture growing at about 21° C.;

Rooting habit: Fleshy, lightly branching, with roots up to 15 cm long;

Root color: Nearest RHS 158C;

Plant shape and habit: Succulent herbaceous perennial with basal rosettes of about 180 leaves radially emerging and slightly arching from central rhizome extending below the base of the plant when grown in containers, producing a radially-symmetrical, rounded mound;

Plant size: Foliage height about 25.0 cm tall from soil line to the top of the leaves and about 45.0 cm wide at the widest point slightly below soil line in container;

Foliage description: Gladiate; simple; margins finely dentate with flexible teeth, teeth about 1.5 mm long and spaced about 2.0 mm apart; apex narrowly acute; base truncate, sessile, clasping; slightly concaved; flattening distally; bi-laterally symmetrical; with dark burgundy spots to about 1.6 cm long and 1.3 cm across;

Leaf size: To about 25.5 cm long, about 3.0 cm wide at base and 3.0 mm thick, average about 23.0 cm long, 2.8 cm wide and 2.5 mm thick;

Foliage fragrance: None observed;

Leaf blade color:

*Adaxial* (*young*).—Nearest RHS 137A with spots intensifying with ultraviolet light exposure to nearest RHS N187A.

*Abaxial* (*young*).—Nearest RHS 138A with spots intensifying with ultraviolet light exposure to nearest RHS N187A.

*Adaxial* (*mature*).—Nearest RHS 137A with glaucous covering overtones of nearest a blend between RHS 122B and RHS 189B and with spots intensifying with ultraviolet light exposure nearest RHS 187A.

*Abaxial* (*mature*).—Nearest RHS 137A with glaucous covering overtones of nearest a blend between RHS 122B and RHS 189B and with longitudinal center portion darker than RHS 144A.

*Teeth*.—Nearest RHS 160C.

Petiole: Sessile;

Veins: Parallel; not distinct abaxial or adaxial;

Peduncle: Terete; glaucous; glabrous; stiff; strong; with cauline leaves nearly adpressed along surface; branched in proximal about 125 cm long before first flower, 86.0 cm long flowering portion and 1.7 cm diameter at base; attitude upwards, erect;

Peduncle color: Base between RHS N187A and RHS N187B, distally developing a slight green undertone of between RHS N138D and RHS N138C;

Pedicel: Terete; glaucous; glabrous; stiff; strong; about 10.0 mm long and 2.5 mm diameter; attitude mostly upright;

Pedicel color: Nearest RHS 138B;

Cauline leaves: About 36 per scape; gladiate to lanceolate; simple, fleshy, glabrous; margins finely dentate with flexible teeth; narrowly apex acute; base truncate, sessile, clasping; proximally to about 12.0 cm long and about 1.8 cm wide at base, decreasing distally; color adaxial and abaxial same as basal leaves;

Buds one day prior to opening: Elongated globose; terminal bulb about 2.0 cm long and about 1.0 cm across; proximal tube about 1.6 cm long and 6.0 mm across; overall about 5.0 cm long;

Bud color: Nearest RHS 138A;

Flower description: Perfect, actinomorphic; from flower base to tip of anthers about 12.0 cm long and opening to about 6.0 cm across; lasting about 3 to 4 days per flower; flowering period about three weeks in late winter in Michigan greenhouse; producing abundant nectar; approximately 100 flowers per scape; attitude mostly upright;

Flower fragrance: Faintly sweet;

Tepals: Six in two sets of three; linear; slightly glaucous abaxial; glabrous both adaxial and abaxial; margin entire; acute apex and fused in basal 15.0 mm; outer set recurved about 180 degrees, about 3.2 cm long, about 7.0 mm wide above fusion point; inner set about 3.3 cm long and 7.0 mm wide at base and partially revolute;

Tepal color: Adaxial nearest RHS 183D, abaxial basal one-half nearest RHS 193D blushed with nearest RHS 183D toward apex and distal margin;

Androecium: Six;

*Filaments*.—Six; stiff, straight, divaricate; about 12.0 cm long and 2.0 mm diameter at base; color between RHS 187B and RHS 187C.

*Anther*.—Dorsifixed; longitudinal; about 17.0 mm long and 2.5 mm diameter before opening; after dehiscence curving backward; color blend between RHS 166A and RHS 183A.

*Pollen*.—Abundant; color nearest RHS 9A.

Gynoecium: Single;

*Style*.—Extending to 8.2 cm long and 2.0 mm diameter at base; color nearest RHS 187B.

*Stigma*.—Globose, apex tri-lobed; about 2.0 mm tall and 2.5 mm across top; color side nearest RHS 187A; top stigmatic surface in tri-pointed star, color between RHS N187A and RHS 202D.

*Ovary*.—Inferior, glaucous, glabrous; oblong; color nearest RHS 139B.

Fruit: Dehiscent, tri-valved, loculicidal capsule; apex abruptly acute; base slightly tapered; about 3.0 cm long and 13 cm across;

Fruit color: When immature nearest RHS N138A; at dehiscence between RHS N199A and RHS N199B;

Seed: Flattened, near round to semi-circular; about 25 per capsule without manual pollination; about 5.0 mm across and about 1.0 mm thick; color between RHS 200A and RHS 202A;

Disease resistance: ×*Mangave* 'Inkblot' has not been observed to be resistant to diseases beyond that which is normal for ×*Mangave, Agave* or *Manfreda*. The plant is xeromorphic and survives well with minimal water once established. The new plant is hardy at least from USDA zone 8b to 10. Full extent of winter hardiness has not been tested.

It is claimed:

1. A new and distinct cultivar of ornamental ×*Mangave* plant named 'Inkblot' as herein described and illustrated, suitable for the garden or as a potted plant in the garden or home.

* * * * *